United States Patent
Chelyapov et al.

(10) Patent No.: US 11,066,643 B2
(45) Date of Patent: Jul. 20, 2021

(54) NATURAL KILLER CELLS WITH ENHANCED VIABILITY, PROLIFERATION AND CYTOTOXICITY FOLLOWING CRYOPRESERVATION

(71) Applicant: The Bio Box, Corona, CA (US)

(72) Inventors: Nickolas Chelyapov, Newport Beach, CA (US); Rafael Gonzalez, Placentia, CA (US)

(*) Notice: Subject to any disclaimer, the term of this patent is extended or adjusted under 35 U.S.C. 154(b) by 0 days.

(21) Appl. No.: 15/931,393

(22) Filed: May 13, 2020

(65) Prior Publication Data

US 2020/0332257 A1    Oct. 22, 2020

Related U.S. Application Data

(62) Division of application No. 14/847,982, filed on Sep. 8, 2015, now Pat. No. 10,760,054.

(60) Provisional application No. 62/097,535, filed on Dec. 29, 2014.

(51) Int. Cl.
*C12N 5/0783*    (2010.01)

(52) U.S. Cl.
CPC ........ *C12N 5/0646* (2013.01); *C12N 2500/40* (2013.01); *C12N 2501/20* (2013.01); *C12N 2501/2312* (2013.01)

(58) Field of Classification Search
CPC .......... C12N 5/0646; C12N 2501/2312; C12N 2500/40; C12N 2501/20
See application file for complete search history.

(56) References Cited

FOREIGN PATENT DOCUMENTS

CN           101333237 A * 12/2008 ............. C07H 21/04
WO    WO-2015181298 A1 * 12/2015 ................ A61P 9/04

OTHER PUBLICATIONS

Ballas et al. Induction of NK Activity in Murine and Human Cells by CpG Motifs in Oligodeoxynucleotides and Bacterial DNA. The Journal of Immunology, 1996, 157: 1840-1845. (Year: 1996).*
Gerosa et al. Differential Effects of Tyrosine Kinase Inhibition in CD69 Antigen Expression and Lytic Activity Induced by rIL-2, rIL-12, and rIFN-αin Human NK Cells. Cellular Immunology. vol. 150, Issue 2, Sep. 1993, pp. 382-390 (Year: 1993).*
Sivori et al. CpG and double-stranded RNA trigger human NK cells by Toll-like receptors: Induction of cytokine release and cytotoxicity against tumors and dendritic cells. PNAS. vol. 101, No. 27: p. 10116-101231 (Year: 2004).*

* cited by examiner

*Primary Examiner* — Taeyoon Kim
(74) *Attorney, Agent, or Firm* — Law Office of Darius Gleason APC

(57) ABSTRACT

The present disclosure generally relates to compositions of NK cells for adoptive transfer. In particular, the disclosure relates to enhancing viability, proliferation and cytotoxicity of feeder-free NK cells following cryopreservation.

8 Claims, 4 Drawing Sheets

Specification includes a Sequence Listing.

```
SEQUENCE LISTING

<160> NUMBER OF SEQ ID NOS: 1

<210> SEQ ID NO 1
<211> LENGTH: 29
<212> TYPE: DNA
<213> ORGANISM: Artificial Sequence
<220> FEATURE:
<223> OTHER INFORMATION: Synthetic Oligodeoxyribonucleotide

<400> SEQUENCE: 1
tcgcgaacgt tcgccgcgtt cgaacgcgg                                       29
```

NATURAL KILLER CELLS WITH ENHANCED VIABILITY, PROLIFERATION AND CYTOTOXICITY FOLLOWING CRYOPRESERVATION

PRIORITY

This application is a divisional of U.S. patent application Ser. No. 14/982,872, filed Sep. 8, 2015, which application claims the benefit of priority to U.S. Provisional Application No. 62/097,535 filed Dec. 29, 2014, whose disclosures are incorporated by reference in their entirety.

FIELD

The present disclosure relates to medical use of immune system cells in adoptive transfer procedures. The present invention relates to increasing the supply of NK cells available for immunotherapy.

BACKGROUND

The human immune system is composed of several tissues that are enriched with white blood cells (WBCs) including bone marrow and lymph nodes. WBCs participate in two layers of immune defense, the innate immune response and the adaptive immune response. The innate immune response is the first line of immune defense and is primarily made up of WBCs from the myeloid lineage including neutrophils, monocytes, eosinophils and basophils. These are early responding cells that stage an initial defense and alert the rest of the immune system of an infection. The second line of immune defense is the adaptive immune system and is primarily made up of WBCs from the lymphoid lineage including B cells and T cells. These cells wait to receive information about the invading pathogen and then mount a targeted response.

Natural Killer (NK) cells are specialized lymphocytes that act in innate immunity. They are critically important in the anti-viral response and patients lacking NK cells have persistent viral infections. NK cells destroy compromised cells by recognizing abnormally low levels of major histocompatibility complex (MHC) I. This capability also makes NK cells potent against tumor cells which similarly lack MHC I markers. NK cells mature in the bone marrow and other lymph tissues then enter circulation in blood. From the blood NK cells seek infected or oncogenic tissues by following a trail of inflammatory cytokines secreted by monocytes and other early responding cells. Exposure of NK cells to cytokines such as interferon (IFN) alpha ($\alpha$), IFN beta ($\beta$), and Interleukin 2, 12, 15, 18 and 21 as well as Tumor Necrosis Factor alpha (TNF $\alpha$) increases NK cytotoxicity by orders of magnitude. Such cytotoxic NK cells respond aggressively by killing infected cells and thereby limiting the spread of infection.

Using lymphocytes for adoptive transfer therapy was first reported over 50 years ago where transplanted T cells conferred immunity to cancer in rodent models. Adoptive T cell transfer involves the isolation of T cells from blood or bone marrow followed by concentration or expansion of the cells in vitro. Once a sufficiently large or concentrated population is obtained the T cells are infused into a patient. More recently clinicians have sought to use NK cells for adoptive transfer because of their ability to recognize and kill tumor cells without requiring any particular tumor cell marker. However development of NK cell adoptive transfer procedures has been impeded by the limited supply of viable cells. NK cells represent only a small fraction of the cells in blood and isolation from a typical blood draw does not yield many cells. Furthermore, NK cells must be purified away from contaminating PBMCs such as T and B cells by CD3 and CD19 depletion, respectively. This is a necessary step for allogenic transplantation where the presence of T and B cells increases risk of graft versus host disease (GVHD) but further reduces the NK cell yield.

In addition, NK cells expand poorly in vitro compared to other kinds of cells due mainly to early senescence. Using even the most effective methods, NK cells are susceptible to telomere shortening and senescence after only a few passages. Among the most effective methods for increasing NK cell viability and proliferation in vitro is co-culturing with feeder cells. Commonly used feeder cells for NK expansion include irradiated peripheral blood mononuclear cells (PBMCs), Epstein-Barr virus-transformed lymphoblastoid cell lines (EBC-LCL), gene-modified K562 cells constitutively expressing IL-15 or 21, and other irradiated tumor cell lines. Co-culturing with feeder cells significantly increases NK cell viability and proliferation with population increases between 1,000 and 50,000 times. Although NK cells grown on feeder cells can be used clinically, feeder cells remain are undesirable because of the increased risk of contamination and the need for additional testing for by bacteria, endotoxin and mycoplasma contamination.

NK cells may be cultured without feeder cells if provided with sufficient cytokines such as IL-2, 12, 15, 18, 21 or nicotinamide. The resulting NK cells exhibit increased cytotoxicity compared to freshly isolated NK cells but can only be expanded between 100 and 300 times. The limited expansion potential is due to telomere loss and senescence. In addition, residual IL-2 can have severe side effects on patients.

A problem related to the short supply and difficulty of expanding NK cells is the fact that they do not tolerate cryopreservation in liquid nitrogen well. The problem is less severe in feeder based systems but remains a serious problem for feeder-free systems. Losses in both viability and cytotoxicity resulting from cryopreservation are only partly rescued by addition of IL-2 to culture media. Cryopreservation of NK cells is a clinical necessity for adoptive transfer immunotherapy because without it only cells freshly isolated from patient blood can be used. Fresh NK cells require a patient to be ready for infusion at a very specific time point after isolation and if that time point is missed, something that frequently occurs with ill patients, the entire procedure must be aborted.

What is needed is an increased supply of NK cells cultured in feeder free systems available for adoptive transfer procedures. The supply of NK cells would be greatly expanded by the ability to efficiently cryopreserve and then later expand NK cells in vitro and restore cytotoxicity without feeder cells and without requiring large quantities of cytokines. Such NK cells would be available to patients on a more flexible basis and remove a barrier to adoptive transfer of NK cells.

SUMMARY

The present disclosure provides NK cells and improved methods for feeder free culture of NK cells following cryopreservation. The method enables increased viability, proliferation and cytotoxicity of NK cells by culturing thawed cells in the presence of short oligodeoxyribonucleotides (ODNs) bearing a CpG dinucleotide repeat motif. The results disclosed herein demonstrate that when NK cells thawed following cryopreservation are cultured without feeder cells in the presence of CpG ODNs they exhibit increased viability, proliferation and cytotoxicity compared to control cells cultured without CpG ODNs.

In one aspect of the present disclosure, NK cells thawed following cryopreservation and cultured without feeder cells in the presence of CpG ODNs have increased viability compared to cells cultured without CpG ODNs.

In another aspect of the present disclosure, NK cells thawed following cryopreservation and cultured without feeder cells in the presence of CpG ODNs have increased proliferation compared to cells cultured without CpG ODNs.

In another aspect of the present disclosure, NK cells thawed following cryopreservation and cultured without feeder cells in the presence of CpG ODNs have increased cytotoxicity compared to cells cultured without CpG ODNs.

In another aspect of the present disclosure, CpG ODNs that may be used according to the method include SEQ ID NO: 1.

In another aspect of the present disclosure, CpG ODNs that may be used according to the method include those which function as pathogen associated molecular patterns.

In another embodiment of the present disclosure, NK cells thawed following cryopreservation and cultured without feeder cells in the presence of CpG ODNs and additionally cultured in the presence of cytokines exhibit additional increases in viability, proliferation and cytotoxicity compared to only CpG ODN supplementation and compared to control cells with no ODN or cytokine supplementation.

In another aspect of the present disclosure cytokines that may optionally be used according to the method include interleukin (IL)-12.

A further object of the present disclosure is to provide NK cells thawed following cryopreservation and cultured without feeder cells in the presence of CpG ODNs that exhibit increased viability, proliferation, and cytotoxicity without requiring large quantities of cytokines.

A further object of the present invention is to provide NK cells thawed following cryopreservation and cultured without feeder cells in the presence of CpG ODNs that exhibit increased viability, proliferation and cytotoxicity to patients on a flexible basis.

BRIEF DESCRIPTION OF THE DRAWINGS

For a more complete understanding of the principles disclosed herein, and the advantages thereof, reference is now made to the following descriptions taken in conjunction with the accompanying drawings in which.

DETAILED DESCRIPTION

Figure 1:
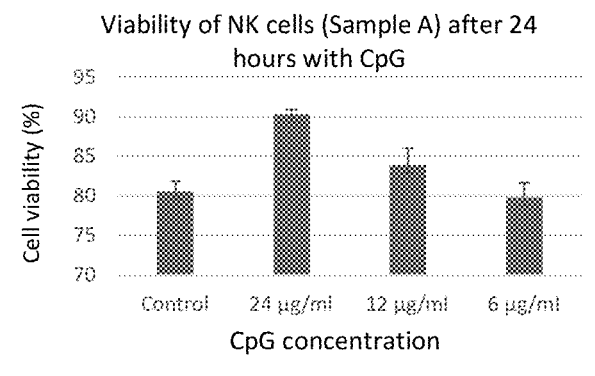
FIG. 1 is a graph showing average cell viability for populations of NK cells (Sample A) 48 hours post thaw, cultured for 24 hours in the presence of CpG ODN.

The present disclosure includes a variety of aspects which may be combined in different ways. The following description are provided to list elements and describe some of the embodiments of the present invention. These elements are listed with initial embodiments, however it should be understood that they may be combined in any manner and in number to create additional embodiments. The variously described examples should not be construed to limit the present disclosure to only the explicitly described systems, techniques, and applications. Further, this description should be understood to support and encompass descriptions and claims of all the various embodiments, systems, techniques, and applications with any number of the disclosed elements, with each element alone, and also with any and all various permutations and combinations of all elements in this or any subsequent application.

In the following examples, Human NK cells were isolated from peripheral blood mononuclear cells (PBMCs) of three donors (Samples A, B and C). In other embodiments NK cells from bone marrow, umbilical cord, or other tissues could be used. After feeder-free in vitro propagation for 2.5 to 3.5 weeks, the cells were frozen and stored in liquid nitrogen. After 3-5 months of cryostorage the cells were thawed and used in the following experiments. In other embodiments longer periods of cryopreservation could be used.

CpG ODNs are short single-stranded synthetic DNA molecules that contain a cytosine deoxyribonucleotide ("C") followed by a guanine deoxyribonucleotide ("G"). The CpG dinucleotide motifs (CpGs) function as pathogen-associated molecular patterns (PAMPs) due to their abundance in microbial genomes and rarity in vertebrate genomes. CpG ODNs are typically in the range of 8 to 40 base pairs in length but may optionally be longer or shorter. NK cells recognize and bind to the ODNs through the Toll-Like Receptors (TLR), including TLR 9 (TLR9) which is a highly conserved gene that acts to recognize PAMPs.

In the following examples the CpG ODN used was SEQ ID NO: 1, a 29-mer deoxyribo-oligonucleotide with-full phosphorothioate modification. In other embodiments other ODN sequences could be used. SEQ ID NO: 1 belongs to Class C CpG ODN-multispecies, has a double stem loop and contains unmethylated CpGs dinucleotides in a sequence context that is recognized by TLR9. In other embodiments other classes of CpG ODNs could be used including class A or B. In still another embodiment the CpG ODN used can be a mixture of sequences. In yet another embodiment, nucleic acids of any size (even many kb long) can be used since larger nucleic acids are degraded into oligonucleotides within cells.

NK cells thawed from liquid nitrogen cryopreservation were counted using an automated cell counter. The trypan blue exclusion assay was used to determination of the proportion of viable NK cells. NK cellular proliferation was determined by cell comparing starting and ending cell counts. Cytotoxicity of NK cells was determined using CYTOTOX 96 Non-Radioactive Cytotoxicity Assay Kit from Promega when a 10:1 ratio of NK cells to K562 target cells was used.

EXAMPLES

Example 1: D-SL03 Alone Increases Viability and Proliferation Rate of NK Cells (Sample A) After Cryopreservation Sample A ($1\times10^6$ cells/ml, viability 89.7% immediately after thawing) was exposed to different concentrations of D-SL03 24 hours after thawing for 24 and 48 hours.

FIG. 1 shows the average viability of cells 48 hours post thaw, and after 24 hours of treatment with D-SL03. The viability of control cells decreased to an average of 80.5%, down from 89.7% at thaw. The viability of cells treated with 24 ug/ml of D-SL03, was 90.3%, or 12.2% greater than that of control cells. The viability of cells treated with 12 ug/ml of D-SL03 was 4% greater than the viability of control cells. The viability of cells treated with 6 ug/ml of D-SL03 showed no increase in viability compared to control cells after 24 hours.

Figure 2:
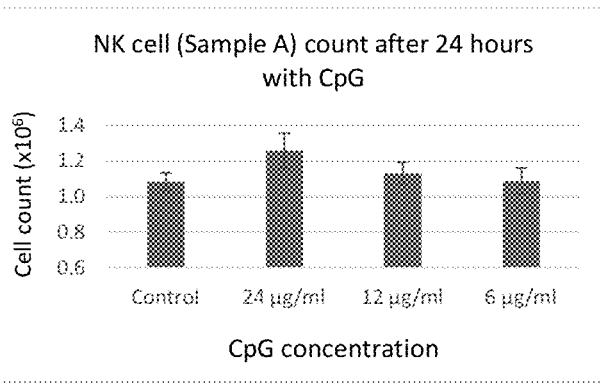
FIG. 2 is a graph showing average cell count/ml for populations of NK cells (Sample A) 48 hours post thaw, cultured for 24 hours in the presence of CpG ODN.

FIG. 2 shows the average number of NK cells/ml 48 hours post thaw and after 24 hours of treatment with D-SL03. The average number of control cells per/ml 48 hours post thaw was 1.08e6 cells/ml. This represents a statistically non-significant increase from the plating number after 24 hours of 1.06e6 cells/ml on the first day. The average number of cells after treatment with 24 ug/ml of D-SL03, was 1.26e6 cells/ml, or 16.7% greater than that of control cells. The average number of cells/ml after treatment with 12 ug/ml of D-SL03 was 4.6% greater (statistically non-significant) than the average number of control cells. The average number of cells after treatment with 6 ug/ml of D-SL03 was 1% greater (statistically non-significant) than that of control cells after 24 hours.

Figure 3:
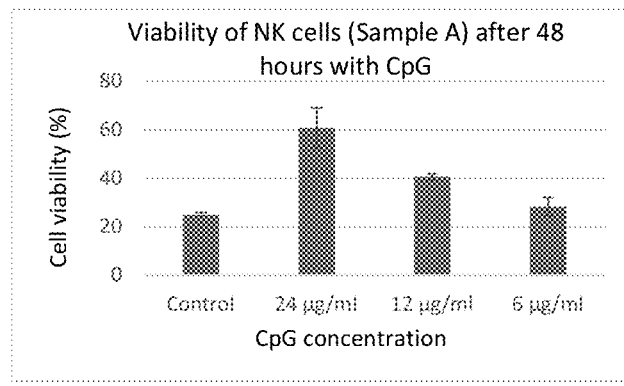
FIG. 3 is a graph showing average cell viability for populations of NK cells (Sample A) 72 hours post thaw, cultured for 48 hours in the presence of CpG ODN.

FIG. 3 shows the average cell viability of the cells 72 hours post thaw, and after 48 hours of treatment with D-SL03. The viability of cells treated with 24 ug/ml of D-SL03, was 143% greater than that of control cells. The viability of cells treated with 12 ug/ml of D-SL03 was 62% greater than the viability of control cells. The viability of cells treated with 6 ug/ml of D-SL03 was 13% greater than the viability of control cells after 48 hours.

Figure 4:
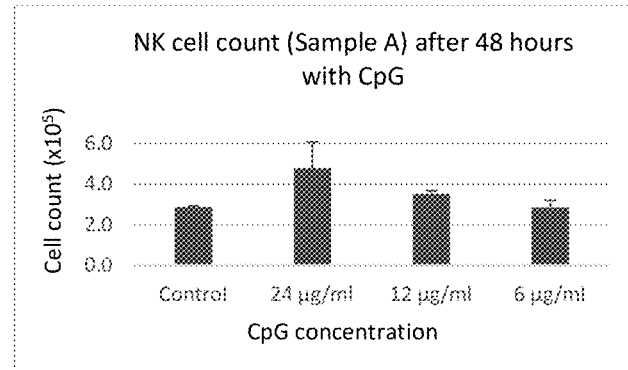
FIG. 4 is a graph showing average cell count/ml for populations of NK cells (Sample A) 72 hours post thaw, cultured for 48 hours in the presence of CpG ODN.

FIG. 4 shows the average number of cells/ml 72 hours post thaw and after 48 hours of treatment with D-SL03. The average number of cells/ml after treatment with 24 ug/ml of D-SL03, was 68% greater than that of control cells. The average number of cells after treatment with 12 ug/ml of D-SL03 was 23.5% greater than the average number of control cells. The average number of cells after treatment with 6 ug/ml of D-SL03 showed no increase over control cells after 48 hours.

These results show that in the absence of CpGs post-thawing, NK cells are prone to low viability and progressive reduction in population size. The results demonstrate that in the presence of D-SL03, NK cell viability after cryopreservation can be increased by as much as 12% after 24 hours and up to 143% after 48 hours compared with control untreated cells. The results also show that the cell population can contain 68% more cells after 48 hours in the presence of D-SL03 versus control cells. These results show the potency of CpG ODN, D-SL03 in particular, to boost NK cell viability following cryopreservation. Based on the data for Sample A, it was concluded that CpG ODN should be applied immediately after thawing to maintain higher cell count and viability. Hence, subsequent experiments were carried out with D-SL03 added to NK cells immediately after thawing.

Example 2: D-SL03 Alone Increases Viability, Proliferation Rate, and Cytotoxicity of NK Cells (Sample B) After Cryopreservation Sample B ($2\times10^6$ cells/ml, viability 89.5% immediately after thawing) was exposed to different concentrations of D-SL03 immediately after thawing for 48 hours.

Figure 5:
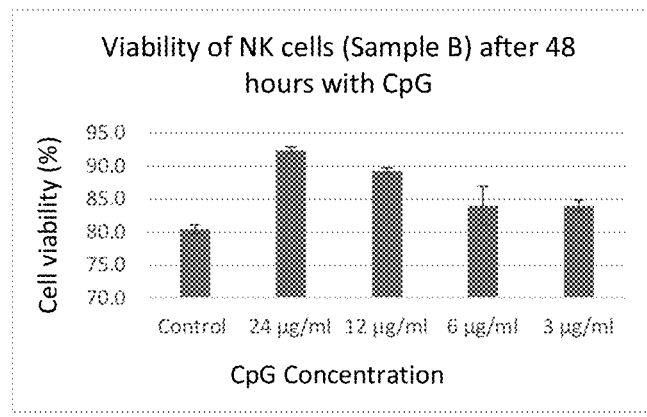
FIG. 5 is a graph showing the average NK cell viability (Sample B) of the cells 48 hours post thaw, cultured for 48 hours in the presence of CpG ODN.

FIG. 5 shows that the viability of control untreated cells after 48 hours in culture decreased to an average of 80.4%, compared at 89.5% after 48 at thaw. The viability of cells treated with 24 ug/ml D-SL03, was 92.4% on average (14.9% increase), 89.3% at 12 ug/ml (11.0% increase) and 84% for both 6 ug/ml and 3 ug/ml of D-SL03, statistically non-significant increase compared with control cells.

Figure 6:
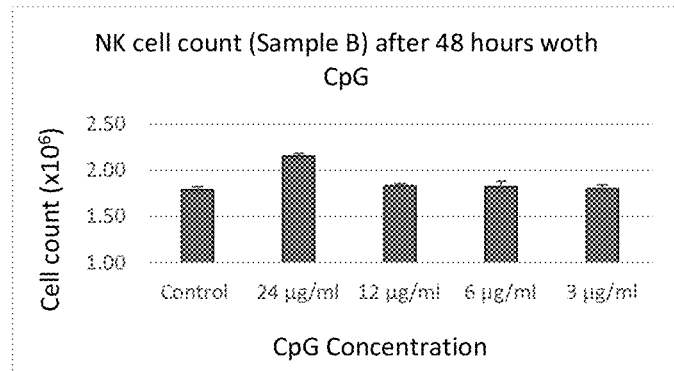
FIG. 6 is a graph showing average cell count/ml for populations of NK cells (Sample B) 48 hours post thaw, cultured for 48 hours in the presence of CpG ODN.

FIG. 6 shows the average number of NK cells/ml48 hours post thaw and incubation with D-SL03. The population sizes of cells treated with 24, 12, 6, and 3 µg/ml of D-SLO3 were 20%, 2.8%, 1.7% and 0.6% greater, with the last 3 numbers being statistically non-significant compared with control cells.

Figure 7:
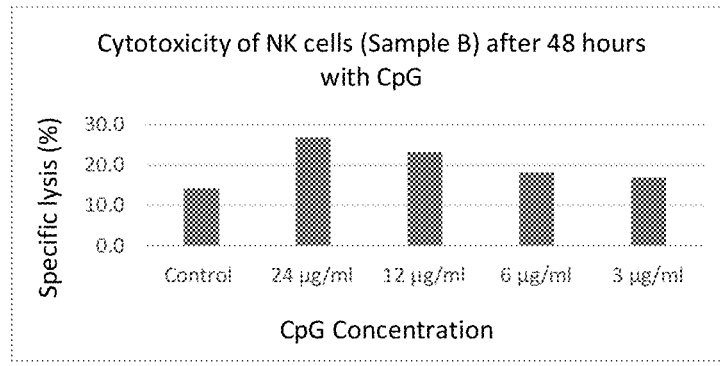
FIG. 7 is a graph showing cytotoxicity for populations of NK cells (Sample B) expressed as specific lysis of target cells by NK cells 48 hours post thaw, cultured for 48 hours in the presence of CpG ODN.

FIG. 7 shows increase in cytotoxicity NK of cells 48 hours post thaw and incubation with D-SL03. The cytotoxicity of NK cells expressed as specific lysis of target cells by NK cells treated with 24, 12, 6, and 3 µg/ml of D-SL03 was 88.7%, 62.6%, 28.2%, and 19.0%, respectively, greater than that of control cells.

The results presented for Sample B where NK cells were incubated with D-SL03 starting immediately after thaw and continuing for 48 hours show that there was no statistically significant drop in viability of control cells as with sample A. Nevertheless, incubation with D-SL03 resulted in statistically significant increase in viability at 24 and 12 µg/ml of D-SL03. A 20% increase in proliferation rate for D-SL03 at 24 µg/ml was also observed. In addition to increased viability and population size, D-SL03 also increased cytotoxicity of NK cells by as much as 88.7% at 24 µg/ml compared with control cells.

Example 3: D-SL03 Plus IL-12 Further Increases Viability, Proliferation Rate, and Cytotoxicity of NK Cells (Sample C) After Cryopreservation Sample C ($2\times10^6$ cells/ml, viability 75.9% immediately after thawing) was exposed to different concentrations of D-SL03 and 1 µg/ml of IL-12 immediately after thawing for 48 hours. Control cells were propagated in the presence of 1 µg/ml of IL-12.

Figure 8:
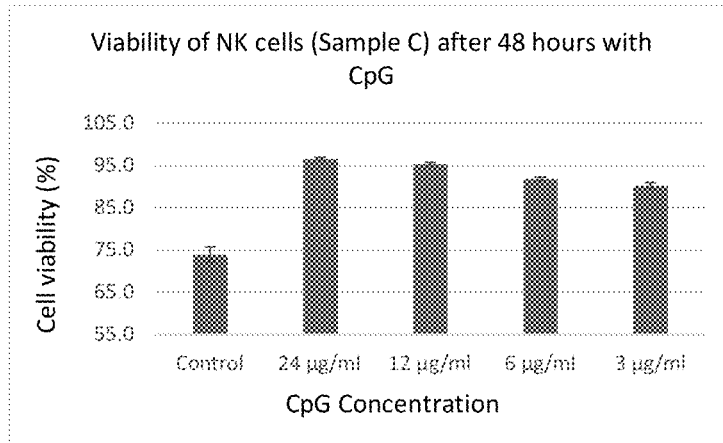
FIG. 8 is a graph showing the average NK cell viability (Sample C) of the cells 48 hours post thaw, cultured for 48 hours in the presence of CpG ODN and IL-12.

FIG. 8 shows that the viability of control cells after 48 hours in culture with immediate after thawing exposure to IL-12 decreased to an average of 73.9%, compared with 75.9% (statistically non-significant decrease) at 48 hours after thawing. The viability of cells treated with 24, 12, 6 and 3 µg/ml of D-SL03, was 30.6%, 28.8%, 24.2%, and 22.0% greater than that of control cells.

Figure 9:
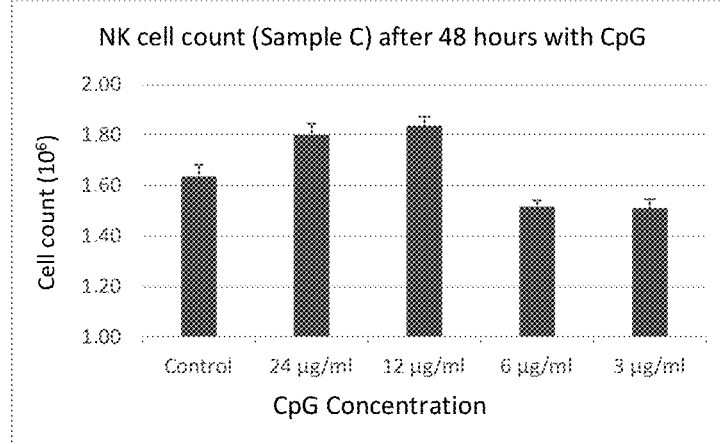
FIG. 9 is a graph showing average cell count/ml for populations of NK cells (Sample C) 48 hours post thaw, cultured for 24 hours in the presence of CpG ODN and IL-12.

FIG. 9 shows the average number of NK cells/ml 48 hours post thaw and incubation with D-SL03 and IL-12. The population sizes of cells treated with 24, 12, 6, and 3 µg/ml of D-SLO3 were 9.8%, 12.2%, greater and there was no statistically significant change, respectively, compared with control cells.

Figure 10:
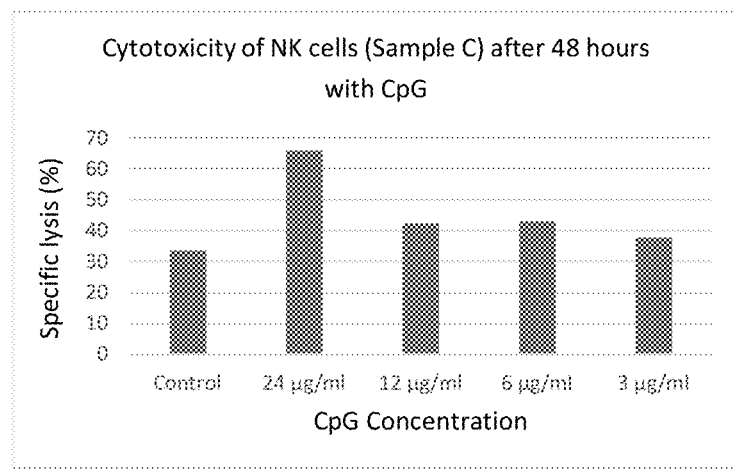
FIG. 10 is a graph showing cytotoxicity for populations of NK cells (Sample C) expressed as specific lysis of target cells by NK cells 48 hours post thaw, cultured for 48 hours in the presence of CpG ODN and IL-12.

FIG. 10 shows increase in cytotoxicity NK of cells 48 hours post thaw and incubation with D-SL03 and IL-12. The cytotoxicity of NK cells expressed as specific lysis of target cells by NK cells treated with 24, 12, 6, and 3 µg/ml of D-SL03 was 97.3%, 26.3%, 28.6%, and 12.8%, respectively, greater than that of control cells. The results presented show that, IL-12 together with D-SL03, has a synergistic effect on NK cell viability compared with Sample B, 30.6% vs 14.9%, but does not boost proliferation. Synergism is also noted for cytotoxicity, 97.3% vs 88.7% without IL-12.

The results with NK cells in Sample C indicate that D-SL03 is a potent booster of NK cell viability, proliferation rate and cytotoxicity in thawed NK cells compared to cells that were not treated with D-SLO3. CpG ODN should be added to NK cells immediately after thawing. IL-12 acts synergistically with D-SL03 in terms of increasing NK cell viability and cytotoxicity.

It will be understood that various modifications can be made to the various embodiments of the present disclosure without departing from the true scope thereof. Therefore, the above description should not be construed as limiting the invention, but merely as an exemplification of preferred embodiments thereof. Those of skill in the art will envision other modifications within the scope and spirit of the present disclosure

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated population of natural killer (NK) cells that are thawed following cryopreservation and cultured without feeder cells in the presence of a CpG oligodeoxyribonucleotide (ODN) having a sequence identical to SEQ ID NO:1 at a concentration of 3 µg/ml to 24 µg/ml; and IL-12 at a concentration of 1 µg/ml, wherein said NK cells were cultured without feeder cells prior to the cryopreservation.

2. The population of claim 1 wherein the CpG ODN functions as a pathogen associated molecular pattern.

3. The population of claim 1 wherein a period of cryopreservation provides flexibility to a patients receiving an NK cell adoptive transfer therapy.

4. The population of claim 1 wherein a combination of CpG ODN and IL-12 acts synergistically on NK cell viability and cytotoxicity.

5. An isolated population of natural killer (NK) cells that are thawed following cryopreservation and cultured without feeder cells in the presence of a CpG oligodeoxyribonucleotide (ODN) having a sequence identical to SEQ ID NO:1 at a concentration of 3 µg/ml to 24 µg/ml; and IL-12 at a concentration of 1 µg/ml, wherein said NK cells were expanded from peripheral blood mononuclear cells without feeder cells prior to the cryopreservation.

6. The population of claim 5 wherein the CpG ODN functions as a pathogen associated molecular pattern.

7. The population of claim 5 wherein a period of cryopreservation provides flexibility to a patients receiving an NK cell adoptive transfer therapy.

8. The population of claim 5 wherein a combination of CpG ODN and IL-12 acts synergistically on NK cell viability and cytotoxicity.

* * * * *